United States Patent
Fink et al.

(10) Patent No.: US 7,946,291 B2
(45) Date of Patent: *May 24, 2011

(54) VENTILATION SYSTEMS AND METHODS EMPLOYING AEROSOL GENERATORS

(75) Inventors: James Fink, San Mateo, CA (US); Ehud Ivri, Newport Beach, CA (US)

(73) Assignee: Novartis AG, Basel (CH)

( * ) Notice: Subject to any disclaimer, the term of this patent is extended or adjusted under 35 U.S.C. 154(b) by 428 days.

This patent is subject to a terminal disclaimer.

(21) Appl. No.: 10/828,765

(22) Filed: Apr. 20, 2004

(65) Prior Publication Data

US 2005/0229927 A1    Oct. 20, 2005

(51) Int. Cl.
*A61M 16/00* (2006.01)
*A61M 16/14* (2006.01)

(52) U.S. Cl. ......... 128/203.12; 128/204.18; 128/204.23; 128/200.14; 128/200.16; 128/200.24

(58) Field of Classification Search ............. 128/203.12, 128/204.18, 204.23, 200.16, 200.14, 200.24
See application file for complete search history.

(56) References Cited

U.S. PATENT DOCUMENTS

| | | |
|---|---|---|
| 550,315 A | 11/1895 | Allen |
| 809,159 A | 1/1906 | Willis et al. |
| 1,680,616 A | 8/1928 | Horst |
| 2,022,520 A | 11/1935 | Philbrick |
| 2,101,304 A | 12/1937 | Wright |
| 2,158,615 A | 5/1939 | Wright |
| 2,187,528 A | 1/1940 | Wing |
| 2,223,541 A | 12/1940 | Baker |
| 2,266,706 A | 12/1941 | Fox et al. |
| 2,283,333 A | 5/1942 | Martin |
| 2,292,381 A | 8/1942 | Klagges |
| 2,360,297 A | 10/1944 | Wing |
| 2,375,770 A | 5/1945 | Dahlberg |
| 2,383,098 A | 8/1945 | Wheaton |
| 2,404,063 A | 7/1946 | Healy |
| 2,430,023 A | 11/1947 | Longmaid |
| 2,474,996 A | 7/1949 | Wallis |
| 2,512,004 A | 6/1950 | Wing |
| 2,521,657 A | 9/1950 | Severy |
| 2,681,041 A | 6/1954 | Zodtner et al. |
| 2,693,178 A * | 11/1954 | Gilroy ..................... 128/200.14 |
| 2,705,007 A | 3/1955 | Gerber |
| 2,735,427 A | 2/1956 | Sullivan |

(Continued)

FOREIGN PATENT DOCUMENTS

CH    477 855    9/1969

(Continued)

OTHER PUBLICATIONS

A. Smedsaas-Löfvenbert, Nebulization of Drugs in a Nasal CPAP System, Scandinavian University Press, 1999, Acta Paediatr 88: 89-92, Sweden.

(Continued)

*Primary Examiner* — Justine R Yu
*Assistant Examiner* — Clinton Ostrup
(74) *Attorney, Agent, or Firm* — Michael J. Mazza

(57) ABSTRACT

A pressure-assisted breathing system comprises a pressure-generating circuit for maintaining a positive pressure within the system, and a patient interface device coupled to a patient's respiratory system. A respiratory circuit is positioned between the pressure-generating circuit and the patient interface device and a nebulizer is coupled to the respiratory circuit.

7 Claims, 6 Drawing Sheets

U.S. PATENT DOCUMENTS

| | | | |
|---|---|---|---|
| 2,764,946 A | 10/1956 | Henderson | |
| 2,764,979 A | 10/1956 | Henderson | |
| 2,779,623 A | 1/1957 | Eisenkraft | |
| 2,935,970 A | 5/1960 | Morse et al. | |
| 3,103,310 A | 9/1963 | Lang | |
| 3,325,031 A | 6/1967 | Singler | |
| 3,411,854 A | 11/1968 | Rosler et al. | |
| 3,490,452 A * | 1/1970 | Greenfield | 128/200.23 |
| 3,515,348 A | 6/1970 | Coffman, Jr. | |
| 3,550,864 A | 12/1970 | East | |
| 3,558,052 A | 1/1971 | Dunn | |
| 3,561,444 A | 2/1971 | Boucher | |
| 3,563,415 A | 2/1971 | Ogle | |
| 3,680,954 A | 8/1972 | Frank | |
| 3,715,432 A * | 2/1973 | Merrill | 514/78 |
| 3,719,328 A | 3/1973 | Hindman | |
| 3,738,574 A | 6/1973 | Guntersdorfer et al. | |
| 3,771,982 A | 11/1973 | Dobo | |
| 3,790,079 A | 2/1974 | Berglund et al. | |
| 3,804,329 A | 4/1974 | Martner | |
| 3,812,854 A * | 5/1974 | Michaels et al. | 128/200.16 |
| 3,838,686 A | 10/1974 | Szekely | |
| 3,842,833 A | 10/1974 | Ogle | |
| 3,865,106 A | 2/1975 | Palush | |
| 3,903,884 A | 9/1975 | Huston et al. | |
| 3,906,950 A | 9/1975 | Cocozza | |
| 3,908,654 A | 9/1975 | Lhoest et al. | |
| 3,950,760 A | 4/1976 | Rauch et al. | |
| 3,951,313 A | 4/1976 | Coniglione | |
| 3,958,249 A | 5/1976 | DeMaine et al. | |
| 3,970,250 A | 7/1976 | Drews | |
| 3,983,740 A | 10/1976 | Danel | |
| 3,993,223 A | 11/1976 | Welker, III et al. | |
| 4,005,435 A | 1/1977 | Lundquist et al. | |
| 4,020,834 A | 5/1977 | Bird | |
| 4,030,492 A | 6/1977 | Simburner | |
| 4,052,986 A | 10/1977 | Scaife | |
| 4,059,384 A | 11/1977 | Holland et al. | |
| D246,574 S | 12/1977 | Meierhoefer | |
| 4,076,021 A | 2/1978 | Thompson | |
| 4,083,368 A | 4/1978 | Freezer | |
| 4,094,317 A | 6/1978 | Wasnich | |
| 4,101,041 A | 7/1978 | Mauro, Jr. et al. | |
| 4,106,503 A | 8/1978 | Rsenthal et al. | |
| 4,109,174 A | 8/1978 | Hodgson | |
| 4,113,809 A | 9/1978 | Abair et al. | |
| D249,958 S | 10/1978 | Meierhoefer | |
| 4,119,096 A | 10/1978 | Drews | |
| 4,121,583 A | 10/1978 | Chen | |
| 4,127,123 A * | 11/1978 | Bird | 128/204.25 |
| 4,159,803 A | 7/1979 | Cameto et al. | |
| 4,207,990 A | 6/1980 | Weiler et al. | |
| 4,210,155 A | 7/1980 | Grimes | |
| 4,226,236 A | 10/1980 | Genese | |
| 4,240,081 A | 12/1980 | Devitt | |
| 4,240,417 A | 12/1980 | Holever | |
| 4,248,227 A | 2/1981 | Thomas | |
| 4,261,512 A | 4/1981 | Zierenberg | |
| D259,213 S | 5/1981 | Pagels | |
| 4,268,460 A | 5/1981 | Boiarski et al. | |
| 4,294,407 A | 10/1981 | Reichl et al. | |
| 4,298,045 A | 11/1981 | Weiler et al. | |
| 4,299,784 A | 11/1981 | Hense | |
| 4,300,546 A | 11/1981 | Kruber | |
| 4,301,093 A | 11/1981 | Eck | |
| 4,319,155 A | 3/1982 | Makai et al. | |
| 4,323,064 A * | 4/1982 | Hoenig et al. | 128/204.21 |
| 4,328,798 A * | 5/1982 | Isaacson | 128/202.27 |
| 4,334,531 A | 6/1982 | Reichl et al. | |
| 4,336,544 A | 6/1982 | Donald et al. | |
| 4,338,576 A | 7/1982 | Takahashi et al. | |
| 4,340,044 A * | 7/1982 | Levy et al. | 128/204.21 |
| 4,368,476 A | 1/1983 | Uehara et al. | |
| 4,368,850 A | 1/1983 | Szekely | |
| 4,374,707 A | 2/1983 | Pollack | |
| 4,389,071 A | 6/1983 | Johnson, Jr. et al. | |
| 4,408,719 A | 10/1983 | Last | |
| 4,428,802 A | 1/1984 | Kanai et al. | |
| 4,431,136 A | 2/1984 | Janner et al. | |
| 4,454,877 A | 6/1984 | Miller et al. | |
| 4,465,234 A | 8/1984 | Maehara et al. | |
| 4,474,251 A | 10/1984 | Johnson, Jr. | |
| 4,474,326 A | 10/1984 | Takahashi | |
| 4,475,113 A | 10/1984 | Lee et al. | |
| 4,479,609 A | 10/1984 | Maeda et al. | |
| 4,484,577 A * | 11/1984 | Sackner et al. | 128/203.28 |
| 4,502,481 A * | 3/1985 | Christian | 128/205.24 |
| 4,512,341 A | 4/1985 | Lester | |
| 4,530,464 A | 7/1985 | Yamamoto et al. | |
| 4,533,082 A | 8/1985 | Maehara et al. | |
| 4,539,575 A | 9/1985 | Nilsson | |
| 4,544,933 A | 10/1985 | Heinzl | |
| 4,546,361 A | 10/1985 | Brescia et al. | |
| 4,550,325 A | 10/1985 | Viola | |
| 4,566,452 A | 1/1986 | Farr | |
| 4,591,883 A | 5/1986 | Isayama | |
| 4,593,291 A | 6/1986 | Howkins | |
| 4,605,167 A | 8/1986 | Maehara | |
| 4,613,326 A | 9/1986 | Szwarc | |
| 4,620,201 A | 10/1986 | Heinzl et al. | |
| 4,628,890 A | 12/1986 | Freeman | |
| 4,632,311 A | 12/1986 | Nakane et al. | |
| 4,658,269 A | 4/1987 | Rezanka | |
| 4,659,014 A | 4/1987 | Soth et al. | |
| 4,677,975 A | 7/1987 | Edgar et al. | |
| 4,678,680 A | 7/1987 | Abowitz | |
| 4,679,551 A | 7/1987 | Anthony | |
| 4,681,264 A | 7/1987 | Johnson, Jr. | |
| 4,693,853 A | 9/1987 | Falb et al. | |
| 4,702,418 A | 10/1987 | Carter et al. | |
| 4,722,906 A | 2/1988 | Guire | |
| 4,753,579 A | 6/1988 | Murphy | |
| 4,773,411 A * | 9/1988 | Downs | 128/204.18 |
| 4,790,479 A | 12/1988 | Matsumoto et al. | |
| 4,793,339 A | 12/1988 | Matsumoto et al. | |
| 4,796,807 A | 1/1989 | Bendig et al. | |
| 4,799,622 A | 1/1989 | Ishikawa et al. | |
| 4,805,609 A | 2/1989 | Roberts et al. | |
| 4,819,629 A | 4/1989 | Jonson | |
| 4,819,834 A | 4/1989 | Thiel | |
| 4,826,080 A | 5/1989 | Ganser | |
| 4,826,759 A | 5/1989 | Guire et al. | |
| 4,828,886 A | 5/1989 | Hieber | |
| 4,843,445 A | 6/1989 | Stemme | |
| 4,849,303 A | 7/1989 | Graham et al. | |
| 4,850,534 A | 7/1989 | Takahashi et al. | |
| 4,852,563 A * | 8/1989 | Gross | 128/202.27 |
| 4,865,006 A | 9/1989 | Nogi et al. | |
| 4,871,489 A | 10/1989 | Ketcham | |
| 4,872,553 A | 10/1989 | Suzuki et al. | |
| 4,877,989 A | 10/1989 | Drews et al. | |
| 4,888,516 A | 12/1989 | Daeges et al. | |
| 4,922,901 A | 5/1990 | Brooks et al. | |
| 4,926,915 A | 5/1990 | Deussen et al. | |
| 4,934,358 A | 6/1990 | Nilsson et al. | |
| 4,951,661 A * | 8/1990 | Sladek | 128/202.27 |
| 4,954,225 A | 9/1990 | Bakewell | |
| 4,957,239 A | 9/1990 | Tempelman | |
| 4,964,521 A | 10/1990 | Wieland et al. | |
| D312,209 S | 11/1990 | Morrow et al. | |
| 4,968,299 A | 11/1990 | Ahlstrand et al. | |
| 4,971,665 A | 11/1990 | Sexton | |
| 4,973,493 A | 11/1990 | Guire | |
| 4,976,259 A | 12/1990 | Higson et al. | |
| 4,979,959 A | 12/1990 | Guire | |
| 4,994,043 A | 2/1991 | Ysebaert | |
| 5,002,048 A | 3/1991 | Makiej, Jr. | |
| 5,002,582 A | 3/1991 | Guire et al. | |
| 5,007,419 A | 4/1991 | Weinstein et al. | |
| 5,016,024 A | 5/1991 | Lam et al. | |
| 5,021,701 A | 6/1991 | Takahashi et al. | |
| 5,022,587 A | 6/1991 | Hochstein | |
| 5,024,733 A | 6/1991 | Abys et al. | |
| 5,046,627 A | 9/1991 | Hansen | |
| 5,062,419 A | 11/1991 | Rider | |
| 5,063,396 A | 11/1991 | Shiokawa et al. | |
| 5,063,922 A * | 11/1991 | Hakkinen | 128/200.16 |

| Patent | Date | Inventor(s) |
|---|---|---|
| 5,073,484 A | 12/1991 | Swanson et al. |
| 5,076,266 A | 12/1991 | Babaev |
| 5,080,093 A | 1/1992 | Raabe et al. |
| 5,080,649 A | 1/1992 | Vetter |
| 5,086,765 A | 2/1992 | Levine |
| 5,086,785 A | 2/1992 | Gentile et al. |
| 5,115,803 A | 5/1992 | Sioutas |
| 5,115,971 A | 5/1992 | Greenspan et al. |
| D327,008 S | 6/1992 | Friedman |
| 5,122,116 A | 6/1992 | Kriesel et al. |
| 5,129,579 A | 7/1992 | Conte |
| 5,134,993 A | 8/1992 | Van Der Linden et al. |
| 5,139,016 A | 8/1992 | Waser |
| 5,140,740 A | 8/1992 | Weigelt |
| 5,147,073 A | 9/1992 | Cater |
| 5,152,456 A | 10/1992 | Ross et al. |
| 5,157,372 A | 10/1992 | Langford |
| 5,164,740 A | 11/1992 | Ivri |
| 5,169,029 A | 12/1992 | Behar et al. |
| 5,170,782 A | 12/1992 | Kocinski |
| 5,180,482 A | 1/1993 | Abys et al. |
| 5,186,164 A | 2/1993 | Raghuprasad |
| 5,186,166 A | 2/1993 | Riggs et al. |
| 5,198,157 A | 3/1993 | Bechet |
| 5,201,322 A | 4/1993 | Henry et al. |
| 5,213,860 A | 5/1993 | Laing |
| 5,217,148 A | 6/1993 | Cater |
| 5,217,492 A | 6/1993 | Guire et al. |
| 5,227,168 A | 7/1993 | Chvapil |
| 5,230,496 A | 7/1993 | Shillington et al. |
| 5,245,995 A | 9/1993 | Sullivan et al. |
| 5,246,012 A * | 9/1993 | Strickland ............... 600/581 |
| 5,248,087 A | 9/1993 | Dressler |
| 5,258,041 A | 11/1993 | Guire et al. |
| 5,261,601 A | 11/1993 | Ross et al. |
| 5,263,992 A | 11/1993 | Guire |
| 5,279,568 A | 1/1994 | Cater |
| 5,297,734 A | 3/1994 | Toda |
| 5,299,739 A | 4/1994 | Takahashi et al. |
| 5,303,854 A | 4/1994 | Cater |
| 5,309,135 A | 5/1994 | Langford |
| 5,312,281 A | 5/1994 | Takahashi et al. |
| 5,313,955 A | 5/1994 | Rodder |
| 5,319,971 A | 6/1994 | Osswald et al. |
| 5,320,603 A | 6/1994 | Vetter et al. |
| 5,322,057 A | 6/1994 | Raabe et al. |
| 5,342,011 A | 8/1994 | Short |
| 5,342,504 A | 8/1994 | Hirano et al. |
| 5,347,998 A | 9/1994 | Hodson et al. |
| 5,348,189 A | 9/1994 | Cater |
| 5,350,116 A | 9/1994 | Cater |
| 5,355,872 A * | 10/1994 | Riggs et al. ............ 128/200.21 |
| 5,357,946 A | 10/1994 | Kee et al. |
| 5,372,126 A | 12/1994 | Blau |
| 5,383,906 A | 1/1995 | Burchett et al. |
| 5,388,571 A | 2/1995 | Roberts et al. |
| 5,392,768 A | 2/1995 | Johansson et al. |
| 5,396,883 A | 3/1995 | Knupp et al. |
| 5,414,075 A | 5/1995 | Swan et al. |
| 5,415,161 A | 5/1995 | Ryder |
| 5,419,315 A | 5/1995 | Rubsamen |
| 5,426,458 A | 6/1995 | Wenzel et al. |
| 5,431,155 A | 7/1995 | Marelli |
| 5,435,282 A | 7/1995 | Haber et al. |
| 5,435,297 A | 7/1995 | Klein |
| 5,437,267 A | 8/1995 | Weinstein et al. |
| 5,443,059 A * | 8/1995 | Koch et al. ............ 128/200.16 |
| 5,445,141 A | 8/1995 | Kee et al. |
| D362,390 S | 9/1995 | Weiler |
| 5,449,502 A | 9/1995 | Igusa et al. |
| 5,452,711 A | 9/1995 | Gault |
| 5,458,135 A | 10/1995 | Patton et al. |
| 5,458,289 A | 10/1995 | Cater |
| 5,474,059 A | 12/1995 | Cooper |
| 5,477,992 A | 12/1995 | Jinks et al. |
| 5,479,920 A | 1/1996 | Piper et al. |
| 5,485,850 A | 1/1996 | Dietz |
| 5,487,378 A | 1/1996 | Robertson et al. |
| 5,489,266 A | 2/1996 | Grimard |
| 5,497,944 A | 3/1996 | Weston et al. |
| D369,212 S | 4/1996 | Snell |
| 5,511,726 A | 4/1996 | Greenspan et al. |
| 5,512,329 A | 4/1996 | Guire et al. |
| 5,512,474 A | 4/1996 | Clapper et al. |
| 5,515,841 A | 5/1996 | Robertson et al. |
| 5,515,842 A | 5/1996 | Ramseyer et al. |
| 5,516,043 A | 5/1996 | Manna et al. |
| 5,518,179 A | 5/1996 | Humberstone et al. |
| 5,529,055 A | 6/1996 | Gueret |
| 5,533,497 A | 7/1996 | Ryder |
| 5,537,997 A * | 7/1996 | Mechlenburg et al. .. 128/204.23 |
| 5,542,410 A | 8/1996 | Goodman et al. |
| 5,549,102 A | 8/1996 | Lintl et al. |
| 5,560,837 A | 10/1996 | Trueba |
| 5,563,056 A | 10/1996 | Swan et al. |
| D375,352 S | 11/1996 | Bologna |
| 5,579,757 A | 12/1996 | McMahon et al. |
| 5,582,330 A | 12/1996 | Iba |
| 5,584,285 A * | 12/1996 | Salter et al. ............... 128/200.21 |
| 5,586,550 A | 12/1996 | Ivri et al. |
| 5,588,166 A | 12/1996 | Burnett |
| 5,601,077 A | 2/1997 | Imbert |
| 5,609,798 A | 3/1997 | Liu et al. |
| 5,632,878 A | 5/1997 | Kitano |
| 5,635,096 A | 6/1997 | Singer et al. |
| 5,637,460 A | 6/1997 | Swan et al. |
| 5,647,349 A | 7/1997 | Ohki et al. |
| 5,653,227 A | 8/1997 | Barnes et al. |
| 5,654,007 A | 8/1997 | Johnson et al. |
| 5,654,162 A | 8/1997 | Guire et al. |
| 5,654,460 A | 8/1997 | Rong |
| 5,657,926 A | 8/1997 | Toda |
| 5,660,166 A | 8/1997 | Lloyd |
| 5,664,557 A | 9/1997 | Makiej, Jr. |
| 5,664,706 A | 9/1997 | Cater |
| 5,665,068 A | 9/1997 | Takamura |
| 5,666,946 A * | 9/1997 | Langenback ............ 128/200.14 |
| 5,670,999 A | 9/1997 | Takeuchi et al. |
| 5,685,491 A | 11/1997 | Marks et al. |
| 5,692,644 A | 12/1997 | Gueret |
| 5,694,923 A * | 12/1997 | Hete et al. ................ 128/204.18 |
| 5,707,818 A | 1/1998 | Chudzik et al. |
| 5,709,202 A | 1/1998 | Lloyd et al. |
| 5,714,360 A | 2/1998 | Swan et al. |
| 5,714,551 A | 2/1998 | Bezwada et al. |
| 5,718,222 A | 2/1998 | Lloyd et al. |
| D392,184 S | 3/1998 | Weiler |
| 5,724,957 A | 3/1998 | Rubsamen et al. |
| 5,744,515 A | 4/1998 | Clapper |
| 5,752,502 A | 5/1998 | King |
| 5,755,218 A | 5/1998 | Johansson et al. |
| 5,758,637 A | 6/1998 | Ivri et al. |
| 5,775,506 A | 7/1998 | Grabenkort |
| 5,788,665 A | 8/1998 | Sekins |
| 5,788,819 A | 8/1998 | Onishi et al. |
| 5,790,151 A | 8/1998 | Mills |
| 5,810,004 A | 9/1998 | Ohki et al. |
| 5,819,730 A | 10/1998 | Stone et al. |
| 5,823,179 A | 10/1998 | Grychowski et al. |
| 5,823,428 A | 10/1998 | Humberstone et al. |
| 5,829,723 A | 11/1998 | Brunner et al. |
| 5,836,515 A | 11/1998 | Fonzes |
| 5,839,617 A | 11/1998 | Cater et al. |
| 5,842,468 A | 12/1998 | Denyer et al. |
| 5,862,802 A | 1/1999 | Bird |
| 5,865,171 A | 2/1999 | Cinquin |
| 5,878,900 A | 3/1999 | Hansen |
| 5,893,515 A | 4/1999 | Hahn et al. |
| 5,894,841 A | 4/1999 | Voges |
| 5,897,008 A | 4/1999 | Hansen |
| 5,910,698 A | 6/1999 | Yagi |
| 5,915,377 A | 6/1999 | Coffee |
| 5,918,637 A | 7/1999 | Fleischman |
| 5,925,019 A | 7/1999 | Ljungquist |
| 5,938,117 A | 8/1999 | Ivri |
| 5,950,619 A | 9/1999 | Van Der Linden et al. |
| 5,954,268 A | 9/1999 | Joshi et al. |
| 5,960,792 A | 10/1999 | Lloyd et al. |

| Patent No. | Date | Inventor(s) |
|---|---|---|
| 5,964,417 A | 10/1999 | Amann et al. |
| 5,970,974 A | 10/1999 | Van Der Linden et al. |
| 5,976,344 A | 11/1999 | Abys et al. |
| 5,993,805 A | 11/1999 | Sutton et al. |
| 6,000,396 A | 12/1999 | Melker et al. |
| 6,007,518 A | 12/1999 | Kriesel et al. |
| 6,012,450 A | 1/2000 | Rubsamen |
| 6,014,970 A | 1/2000 | Ivri et al. |
| 6,014,972 A * | 1/2000 | Sladek .................. 128/203.12 |
| 6,026,809 A | 2/2000 | Abrams et al. |
| 6,029,666 A | 2/2000 | Aloy et al. |
| 6,032,665 A | 3/2000 | Psaros |
| 6,037,587 A | 3/2000 | Dowell et al. |
| 6,039,696 A | 3/2000 | Bell |
| 6,045,215 A | 4/2000 | Coulman |
| 6,045,874 A | 4/2000 | Himes |
| 6,047,818 A | 4/2000 | Warby et al. |
| 6,055,869 A | 5/2000 | Stemme et al. |
| 6,060,128 A | 5/2000 | Kim et al. |
| 6,062,212 A | 5/2000 | Davison et al. |
| 6,068,148 A | 5/2000 | Weiler |
| 6,085,740 A | 7/2000 | Ivri et al. |
| 6,096,011 A | 8/2000 | Trombley, III et al. |
| 6,105,877 A | 8/2000 | Coffee |
| 6,106,504 A | 8/2000 | Urrutia |
| 6,116,234 A | 9/2000 | Genova et al. |
| 6,123,413 A | 9/2000 | Agarwal et al. |
| 6,139,674 A | 10/2000 | Markham et al. |
| 6,142,146 A | 11/2000 | Abrams et al. |
| 6,145,963 A | 11/2000 | Pidwerbecki et al. |
| 6,146,915 A | 11/2000 | Pidwerbecki et al. |
| 6,152,130 A | 11/2000 | Abrams et al. |
| 6,155,676 A | 12/2000 | Etheridge et al. |
| 6,158,431 A | 12/2000 | Poole |
| 6,161,536 A | 12/2000 | Redmon et al. |
| 6,163,588 A | 12/2000 | Matsumoto et al. |
| 6,182,662 B1 | 2/2001 | McGhee |
| 6,186,141 B1 | 2/2001 | Pike et al. |
| 6,196,218 B1 | 3/2001 | Voges |
| 6,196,219 B1 | 3/2001 | Hess et al. |
| 6,205,999 B1 | 3/2001 | Ivri et al. |
| 6,216,916 B1 | 4/2001 | Maddox et al. |
| 6,223,746 B1 | 5/2001 | Jewett et al. |
| 6,235,177 B1 | 5/2001 | Borland et al. |
| 6,254,219 B1 | 7/2001 | Agarwal et al. |
| 6,269,810 B1 * | 8/2001 | Brooker et al. .......... 128/203.12 |
| 6,270,473 B1 | 8/2001 | Schwebel |
| 6,273,342 B1 | 8/2001 | Terada et al. |
| 6,318,640 B1 | 11/2001 | Coffee |
| 6,328,030 B1 | 12/2001 | Kidwell et al. |
| 6,328,033 B1 | 12/2001 | Avrahami |
| 6,341,732 B1 | 1/2002 | Martin et al. |
| 6,358,058 B1 | 3/2002 | Strupat et al. |
| 6,394,363 B1 | 5/2002 | Arnott et al. |
| 6,402,046 B1 | 6/2002 | Loser |
| 6,405,934 B1 | 6/2002 | Hess et al. |
| 6,427,682 B1 | 8/2002 | Klimowicz et al. |
| 6,443,146 B1 | 9/2002 | Voges |
| 6,443,366 B1 | 9/2002 | Hirota et al. |
| 6,467,476 B1 | 10/2002 | Ivri et al. |
| 6,467,477 B1 * | 10/2002 | Frank et al. .............. 128/203.23 |
| 6,530,370 B1 * | 3/2003 | Heinonen ................ 128/200.16 |
| 6,539,937 B1 * | 4/2003 | Haveri ..................... 128/200.21 |
| 6,540,153 B1 | 4/2003 | Ivri |
| 6,540,154 B1 | 4/2003 | Ivri et al. |
| 6,543,443 B1 | 4/2003 | Klimowicz et al. |
| 6,546,927 B2 | 4/2003 | Litherland et al. |
| 6,550,472 B2 | 4/2003 | Litherland et al. |
| 6,554,201 B2 | 4/2003 | Klimowicz et al. |
| 6,581,595 B1 | 6/2003 | Murdock et al. |
| 6,581,600 B2 * | 6/2003 | Bird ........................ 128/205.24 |
| 6,615,824 B2 * | 9/2003 | Power ..................... 128/200.14 |
| 6,629,646 B1 | 10/2003 | Ivri |
| 6,640,804 B2 | 11/2003 | Ivri |
| 6,651,650 B1 | 11/2003 | Yamamoto et al. |
| 6,688,304 B2 | 2/2004 | Gonda et al. |
| 6,705,315 B2 | 3/2004 | Sullivan et al. |
| 6,705,316 B2 * | 3/2004 | Blythe et al. ............ 128/204.18 |
| 6,725,858 B2 * | 4/2004 | Loescher ................. 128/200.14 |
| 6,732,944 B2 | 5/2004 | Litherland et al. |
| 6,745,768 B2 | 6/2004 | Colla et al. |
| 6,745,770 B2 | 6/2004 | McAuliffe et al. |
| 6,755,189 B2 | 6/2004 | Ivri et al. |
| 6,769,626 B1 | 8/2004 | Haveri |
| 6,782,886 B2 | 8/2004 | Narayan et al. |
| 6,810,876 B2 | 11/2004 | Berthon-Jones |
| 6,814,071 B2 | 11/2004 | Klimowicz et al. |
| 6,817,361 B2 | 11/2004 | Berthon-Jones et al. |
| 6,840,240 B1 | 1/2005 | Berthon-Jones et al. |
| 6,845,770 B2 | 1/2005 | Klimowicz et al. |
| 6,851,626 B2 | 2/2005 | Patel et al. |
| 6,860,268 B2 * | 3/2005 | Bohn et al. .............. 128/206.21 |
| 6,904,906 B2 * | 6/2005 | Salter et al. ............. 128/200.21 |
| 7,101,341 B2 * | 9/2006 | Tsukashima et al. ......... 600/532 |
| 2001/0013554 A1 | 8/2001 | Borland et al. |
| 2001/0015737 A1 | 8/2001 | Truninger et al. |
| 2002/0002975 A1 * | 1/2002 | Power ..................... 128/203.12 |
| 2002/0011247 A1 | 1/2002 | Ivri et al. |
| 2002/0023650 A1 | 2/2002 | Gunaratnam et al. |
| 2002/0033178 A1 | 3/2002 | Farrell et al. |
| 2002/0036601 A1 | 3/2002 | Puckeridge et al. |
| 2002/0078958 A1 | 6/2002 | Stenzler |
| 2002/0104530 A1 | 8/2002 | Ivri et al. |
| 2002/0121274 A1 | 9/2002 | Borland et al. |
| 2002/0134372 A1 | 9/2002 | Loeffler et al. |
| 2002/0134374 A1 | 9/2002 | Loeffler et al. |
| 2002/0134375 A1 | 9/2002 | Loeffler et al. |
| 2002/0134377 A1 | 9/2002 | Loeffler et al. |
| 2002/0162551 A1 | 11/2002 | Litherland |
| 2002/0162553 A1 * | 11/2002 | Hamilton et al. ......... 128/204.18 |
| 2002/0195107 A1 | 12/2002 | Smaldone |
| 2003/0140921 A1 | 7/2003 | Smith et al. |
| 2003/0145859 A1 | 8/2003 | Bohn et al. |
| 2003/0150445 A1 | 8/2003 | Power et al. |
| 2003/0150446 A1 | 8/2003 | Patel et al. |
| 2003/0226906 A1 | 12/2003 | Ivri |
| 2004/0000598 A1 | 1/2004 | Ivri |
| 2004/0004133 A1 | 1/2004 | Ivri et al. |
| 2004/0011358 A1 | 1/2004 | Smaldone et al. |
| 2004/0035413 A1 | 2/2004 | Smaldone et al. |
| 2004/0035490 A1 | 2/2004 | Power |
| 2004/0050947 A1 | 3/2004 | Power et al. |
| 2004/0139963 A1 | 7/2004 | Ivri et al. |
| 2004/0139968 A1 | 7/2004 | Loeffler et al. |
| 2004/0188534 A1 | 9/2004 | Litherland et al. |
| 2004/0194783 A1 | 10/2004 | McAuliffe et al. |
| 2004/0210153 A1 * | 10/2004 | Tsukashima et al. ......... 600/532 |
| 2004/0226561 A1 | 11/2004 | Colla et al. |
| 2004/0226566 A1 | 11/2004 | Gunaratnam et al. |
| 2004/0256488 A1 | 12/2004 | Loeffler et al. |
| 2005/0011514 A1 | 1/2005 | Power et al. |
| 2005/0039746 A1 * | 2/2005 | Grychowski et al. .... 128/204.18 |
| 2005/0139211 A1 * | 6/2005 | Alston et al. ............. 128/200.14 |
| 2005/0150496 A1 | 7/2005 | Smaldone |
| 2005/0211245 A1 | 9/2005 | Smaldone et al. |
| 2005/0211253 A1 | 9/2005 | Smaldone et al. |
| 2005/0220763 A1 | 10/2005 | Condos et al. |
| 2005/0235987 A1 | 10/2005 | Smaldone et al. |
| 2005/0284469 A1 | 12/2005 | Tobia et al. |

FOREIGN PATENT DOCUMENTS

| | | |
|---|---|---|
| CH | 555 681 | 11/1974 |
| DE | 11 03 522 | 3/1961 |
| DE | 3513628 C1 * | 10/1986 |
| EP | 0 049 636 A1 | 4/1982 |
| EP | 0 103 161 A2 | 3/1984 |
| EP | 0 134 847 A1 | 3/1985 |
| EP | 0 178 925 A2 | 4/1986 |
| EP | 0 387 222 A1 | 9/1990 |
| EP | 0 432 992 A1 | 6/1991 |
| EP | 0 476 991 B1 | 3/1992 |
| EP | 0 480 615 A1 | 4/1992 |
| EP | 0 510 648 A2 | 10/1992 |
| EP | 0 516 565 A1 | 12/1992 |
| EP | 0 542 723 A2 | 5/1993 |
| EP | 0 933 138 A2 | 4/1999 |
| EP | 0 923 957 A1 | 6/1999 |
| EP | 1 142 600 A1 | 10/2001 |

| | | |
|---|---|---|
| GB | 973 458 | 10/1964 |
| GB | 1 454 597 | 11/1976 |
| GB | 2 073 616 A | 10/1981 |
| GB | 2 101 500 | 1/1983 |
| GB | 2 177 623 A | 1/1987 |
| GB | 2 240 494 A | 7/1991 |
| GB | 2 272 389 A | 5/1994 |
| JP | 57-023852 | 2/1982 |
| JP | 57-105608 | 7/1982 |
| JP | 58-061857 | 4/1983 |
| JP | 58-139757 | 8/1983 |
| JP | 59-142163 A | 8/1984 |
| JP | 60-004714 | 1/1985 |
| JP | 61-008357 A | 1/1986 |
| JP | 61-215059 A | 9/1986 |
| JP | 02-135169 | 5/1990 |
| JP | 02-189161 | 7/1990 |
| JP | 60-07721 A | 1/1994 |
| WO | WO 82/03548 | 10/1982 |
| WO | WO 92/07600 A1 | 5/1992 |
| WO | WO 92/11050 A1 | 9/1992 |
| WO | WO 92/17231 A1 | 10/1992 |
| WO | WO 93/01404 A1 | 1/1993 |
| WO | WO 93/10910 A1 | 6/1993 |
| WO | WO 94/09912 A1 | 5/1994 |
| WO | WO 96/09229 | 3/1996 |
| WO | WO 99/17888 | 4/1999 |
| WO | WO 00/37132 | 6/2000 |

OTHER PUBLICATIONS

G. Jorch, Letter to the Editor, Surfactant Aerosol Treatment of Respiratory Distress Syndrome in Spontaneously Breathing Premature Infants, Pediatric Pulmonology 24: 222-224, 1997, Wiley-Liss, Inc.

E. Berggren, Pilot Study of Nebulized Surfactant Therapy for Neonatal Respiratory Distress Syndrome, Acta Paediatr 89: 460-464, Taylor & Francis, ISSN 0803-5253, 2000, Sweden.

G. C. Smaldone, Aerosolized Antibiotics: Current and Future, Respiratory Care, vol. 45, No. 8, pp. 687-675.

Duarte, Alexander G. et al. "Inhalation Therapy During Mechanical Ventialation" Respiratory Care Clinics of North America, Aerosol Therapy, Jun. 2001, pp. 233-259, vol. 7, No. 2.

Fink, James B. et al. "Aerosol Therapy in Mechanically Ventilated Patients: Recent Advances and New Techniques". Seminars in Respiratory and Critical Care Medicine, 2000, pp. 183-201, vol. 21, No. 3.

Fink, James B. et al. Diagram from and abstract of article entitled "Optimizing efficiency of nebulizers during mechanical ventilation: The effect of placement and type of ventilator circuit" Chest, Oct. 1999, 116:312S.

Abys, J.A. et al., "Annealing Behavior of Palladium-Nickel Alloy Electrodeposits," Plating and Surface Finishing, Aug. 1996, pp. 1-7.

Allen, T. *Particle Size Measurement*, Third Edition, Chapman and Hall pp. 167-169 (1981).

Ashgriz, N. et al. "Development of a Controlled Spray Generator" Rev. Sci. lnstrum., 1987, pp. 1291-1296, vol. 58, No. 7.

Berglund, R.N., et al. "Generation of Monodisperse Aerosol Standards" Environ. Sci. Technology, Feb. 1973, pp. 147-153, vol. 7, No. 2.

Cipolla, D.C. et al., "Assessment of Aerosol Delivery Systems for Recombinant Human Deoxyribonuclease," S.T.P. Pharma Sciences 4 (1) 50-62, 1994.

Cipolla, D.C. et al., "Characterization of Aerosols of Human Recombinant Deoxyribonuclease I (rhDNase) Generated by Neulizers, " Pharmaceutical Research II (4) 491-498, 1994.

Dogan, Aydin PhD, Thesis: "Flexional 'Moonie and Cymbal' Actuators", Penn State University, 1994.

Fink, James B. et al. "Aerosol Drug Therapy," Clinical Practice in Respiratory Care; Chapter 12, pp. 308-342; 1999.

Gaiser Tool Company catalog, pp. 26, 29-30 (1990).

Gonda, I. "Therapeutic Aerosols," Pharmaceutics, The Science of Dosage Form Design, Editor: M.E. Aulton, 341-358, 1988.

Hancock, B.C. et al., "Molecular Mobility of Amorphous Pharmaceutical Solids Below Their Glass Transition Temperatures," Pharmaceutical Research 12, 799-806 (1995).

Heyder, J. et al., "Deposition of particles in the human respiratory tract in the size range 0.005-15 microns." J Aerosol Sci 17: 811-825, 1986.

Hickey, Anthony J. "Pharmaceutical Inhalation Aerosol Technology," Drugs and The Pharmaceutical Science, 1992, pp. 172-173, vol. 54.

Hikayama, H., et al. "Ultrasonic Atomizer with Pump Function" Tech. Rpt. IEICE Japan US88-74:25 (1988).

Maehara, N. et al. "Atomizing rate control of a multi-pinhole-plate ultrasonic atomizer" J. Acoustical Soc. Japan, 1988, pp. 116-121, 44:2.

Maehara, N. et al. "Influence of the vibrating system of a multipinhole-plate ultrasonic nebulizer on its performance" Review of Scientific Instruments, Nov. 1986, p. 2870-2876, vol. 57, No. 1.

Maehara, N. et al. "Influences of liquid's physical properties on the characteristics of a multi-pinhole-plate ultrasonic atomizer" J. Acoustical Soc. Japan 1988, pp. 425-431, 44:6.

Maehara, N. et al. "Optimum Design Procedure for Multi-Pinhole-Plate Ultrasonic Atomizer" Japanese Journal of Applied Physics, 1987, pp. 215-217, vol. 26, Supplement 26-1.

Nogi, T. et al. "Mixture Formation of Fuel Injection System in Gasoline Engine" Nippon Kikai Gakkai Zenkoku Taikai Koenkal Koen Ronbunshu 69:660-662 (1991).

Palla Tech Pd an.Pd Alloy Processes—Procedure for the Analysis of Additive IVS in Palla Tech Plating Solutions by HPLC, Technical Bulletin, Electroplating Chemicals & Services, 029-A, Lucent Technologies., pp. 1-5, 1996.

Siemens, "Servo Ultra Nebulizer 345 Operating Manual," pp. 1-23.

TSI Incorporated product catalog. Vibrating Orifice Aerosol Generator (1989).

Ueha, S., et al. "Mechanism of Ultrasonic Atomization Using a Multi-Pinhole Plate" J. Acoust. Soc. Jpn., 1985, pp. 21-26, (E)6,1.

Wehl, Wolfgang R. "Ink-Jet.Printing: The Present State of the Art" for Siemens AG, 1989.

Chinese Office Action Summary from application No. 200580016901.9 issued on Dec. 1, 2010.

* cited by examiner

VENTILATION SYSTEMS AND METHODS EMPLOYING AEROSOL GENERATORS

BACKGROUND OF THE INVENTION

This invention relates to apparatus and methods for delivering medication to the respiratory system of a patient through an invasive or noninvasive pressure-assisted breathing system. More specifically, one aspect of the invention is directed to apparatus and methods for coupling an aerosol generator (nebulizer) with a continuous positive pressure airway ("CPAP") or bi-level positive airway pressure ("Bi-level") system. The use of CPAP and Bi-level systems and therapies are conventional forms of non-invasive ventilation treatment for respiratory disorders in adults, e.g. obstructive sleep apnea and respiratory insufficiency, and in children, e.g. abnormal breathing resulting from small or collapsible airways, small lung volumes, muscle weakness, respiratory distress syndrome, persistent obstruction following surgery, etc. Systems that utilize an endotracheal or tracheotomy tube are examples of invasive pressure-assisted breathing systems. As used herein, the term "pressure-assisted breathing system" is intended to include non-invasive systems such as CPAP and Bi-level systems, as well as invasive systems.

Pressure-assisted breathing systems utilize positive pressure during inhalation to increase and maintain lung volumes and to decrease the work of breathing by a patient. The positive pressure effectively dilates the airway and prevents its collapse. The delivery of positive airway pressure is accomplished through the use of a positive air flow source ("flow generator") that provides oxygen or a gas containing oxygen through a flexible tube connected to a patient interface device such as nasal prongs (cannula), nasopharyngeal tubes or prongs, an endotracheal tube, mask, etc. CPAP devices typically maintain and control continuous positive airway pressure by using a restrictive air outlet device, e.g. a fixed orifice or threshold resistor, or a pressure valve, that modulates the amount of gas leaving the circuit to which the patient interface device is attached. This pressure regulating device may be placed at, before or beyond the patient interface device and defines a primary pressure-generating circuit. During the course of CPAP therapy, the patient may inhale only a fraction of the total flow of gas passing through the primary pressure-generating circuit.

Bi-level systems deliver continuous positive airway pressure but also have the capability to sense when an inspiratory and expiratory effort is being made by the patient. In response to those efforts, Bi-level systems deliver a higher level of inspiratory pressure (IPAP) to keep the airway open and augment inspiratory volumes as a patient breathes in to reduce the work of inhalation, and deliver a lower expiratory pressure (EPAP) as the patient exhales to keep the airway and lungs open during exhalation. Thus, a Bi-level device employs pressure sensors and variable pressure control devices to deliver at least two levels of air pressure that are set to coincide with the patient's inspiratory and expiratory efforts. Bi-level has been found to be useful for a wider range of respiratory disorders than using CPAP alone, particularly in infants and small children.

An aerosol generator or nebulizer has been used to deliver an aerosol of medication through a ventilation device into the respiratory system of a patient. For example, U.S. Pat. No. 6,615,824, issued Sep. 9, 2003, and in co-pending U.S. patent application Ser. No. 10/465,023, filed Jun. 18, 2003, and Ser. No. 10/284,068, filed Oct. 30, 2002 describe apparatus and methods for connecting a nebulizer to a ventilator circuit to emit a medicament directly into the flow of gas being delivered to a patient's respiratory system.

Use of a nebulizer in connection with a pressure-assisted breathing system having a positive pressure-generating circuit with continuous flow through the circuit, such as many CPAP and Bi-level systems, presents certain challenges. Hence, this invention is related generally to addressing such challenges.

BRIEF SUMMARY OF THE INVENTION

The present invention provides a pressure-assisted breathing system comprising, in one configuration, a pressure-generating circuit for maintaining a positive pressure within the system, a patient interface device, a respiratory circuit for providing gas communication between the pressure-generating circuit and the patient interface device, and a nebulizer coupled to the respiratory circuit.

In one embodiment of the invention, the pressure-generating circuit may comprise a conduit that couples a flow generator that produces a high volume flow of gas through the conduit with a pressure-regulating device that maintains the CPAP. The respiratory circuit provides a lower-volume positive pressure air flow from the pressure generating-circuit to the patient interface device for inhalation by the patient. The respiratory circuit may comprise a conduit connected at one end to the pressure-generating circuit and at the other end to the patient interface device. In one particular embodiment, the respiratory circuit comprises a flexible tube having a small diameter, e.g. an outside diameter of 5 mm or less, connected at one end, e.g. through a "T" or "Y" shaped junction unit, to a larger flexible tube comprising the pressure-generating circuit, and at the other end to the patient interface device. This arrangement allows the patient to move his/her head freely without disconnecting the patient interface device from the patient. Alternatively, the respiratory circuit may comprise a gas conduit contained within the patient interface device itself.

The nebulizer is coupled to the respiratory circuit and is adapted to emit an aerosolized medicament directly into the portion of the total gas flow that is inhaled by the patient, preferably in the direct vicinity of the patient's nose, mouth or artificial airway, thereby eliminating the dilution effect caused by introducing the aerosolized medicament into the high-volume gas flow of the pressure-generating circuit. Nebulizers suitable for the practice of the present invention generally comprise a reservoir for holding a liquid medicament to be delivered to a patient's respiratory system, a vibrating aperture-type aerosol generator for aerosolizing the liquid medicament and a connector for connecting nebulizer to the respiratory circuit. Particularly preferred nebulizers of the invention are small and light-weight, for example having a net weight (without liquid) of 5 gms or less, preferably 3 gms or less, and have a connector adapted to attach to the weaker smaller diameter tube making up the respiratory circuit. Such "miniature" nebulizers may have a small reservoir that holds one unit dose of medicament, e.g. less than 4 ml of liquid, and a light-weight aerosol generator, e.g. on the order of about 1 gm in weight. In addition, preferred nebulizers are quiet in operation, e.g. producing less than 5 decibels of sound pressure, so that they can conveniently be placed very close to the patient.

The present invention also provides a method of respiratory therapy comprising the steps of providing a pressure-assisted breathing system having a pressure-generating circuit for providing positive airway pressure and a respiratory circuit coupled to the pressure-generating circuit for providing a flow of gas to a patient's respiratory system, and introducing an aerosolized medicament only into the flow of gas in the respiratory circuit. The present invention also provides a method of delivering a surfactant medicament to a patient's respiratory system.

The present invention provides a number of benefits. The nebulizer of the present invention is located outside the primary high flow pressure-generating circuit of the pressure-assisted breathing system, thereby minimizing the dilution effect that would occur if the aerosolized medicament is introduced into the total (much greater) flow of gas passing through the primary pressure-generating circuit. In addition, because of its small size and quiet operation, the nebulizer may be located in very close proximity to the patient's airway, thereby decreasing the distance which the medicament must travel and further increasing the efficiency of the system.

Due to the increased efficiency of the present invention, the reservoir of the nebulizer may be sized to accommodate a smaller amount of medicament. For example, the reservoir of the nebulizer may have a capacity equal to a single unit dose of medicament, i.e. an amount sufficient for one treatment, and substantially all of the medicament may be delivered to the patient without the need to replenish the reservoir. This is particularly beneficial in respiratory therapies that utilize phospholipid surfactants since these medicaments are scarce, expensive and, because of their high viscosity, difficult to deliver. The present invention may also eliminate the need to pump medicament from an outside container to the nebulizer, although in some applications of the invention this may be desirable.

DETAILED DESCRIPTION OF THE INVENTION

The following detailed description is directed to a CPAP embodiment of the invention for illustrative purposes only, it being understood that the invention is not limited to such embodiment and can be applied to other pressure-assisted breathing systems.

Figure 1:
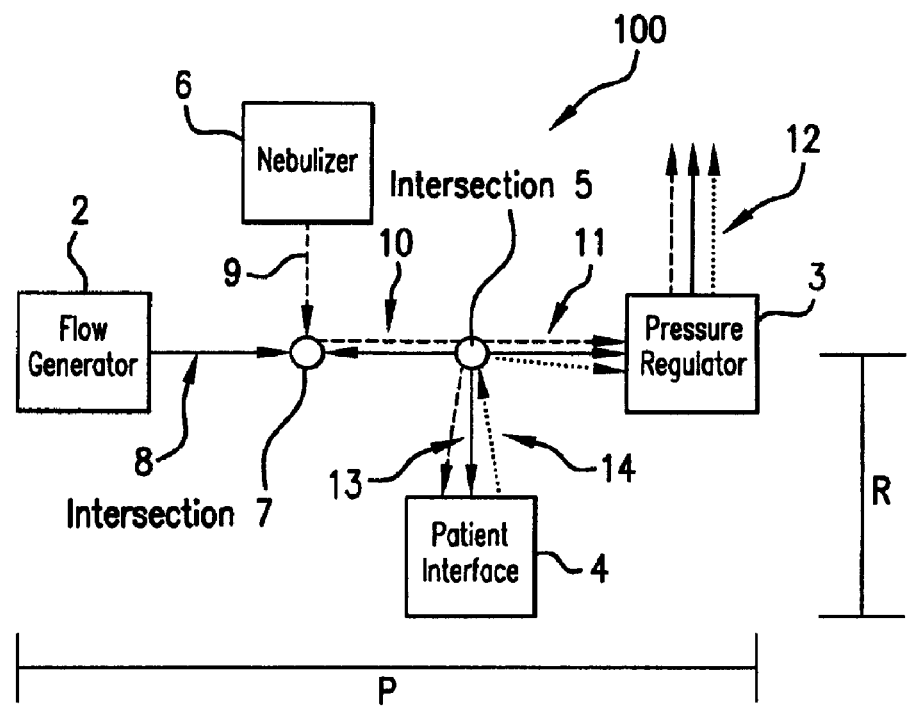
FIG. 1 is a schematic illustration of one embodiment of a CPAP system with a nebulizer.
Figure 2:
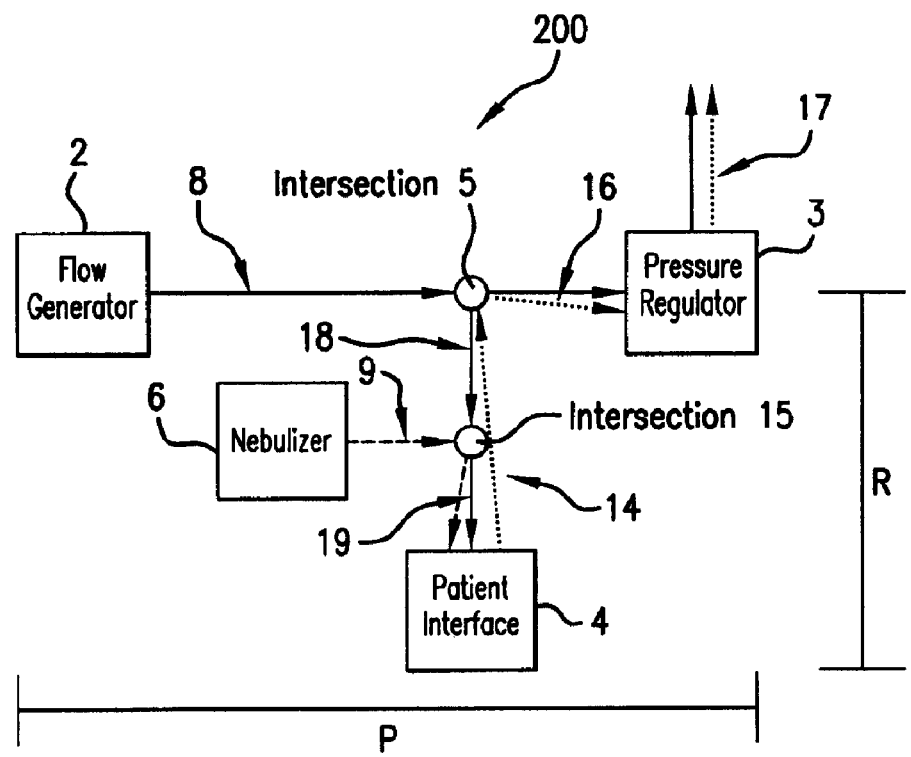
FIG. 2 is a schematic illustration of another embodiment of a CPAP system of the present invention.

FIG. 1 of the drawings is a schematic illustration of a CPAP system 100 employing a nebulizer. The CPAP system 100 includes a primary pressure-generating circuit P and a respiratory circuit R. Circuit P includes a flow generator 2 in fluid communication with a pressure-regulating device 3. Respiratory circuit R includes a patient interface device 4 in fluid communication with circuit P at intersection 5. Nebulizer 6 is in fluid communication with circuit P at intersection 7 upstream to intersection 5. In operation, a high volume flow of gas 8 is introduced into circuit P from flow generator 2 and passes to and through pressure-regulating device 3 so as to maintain a positive pressure in the system. Nebulizer 6 emits an aerosolized medicament 9 into gas flow 8 at intersection 7 to produce combined gas flow 10 containing medicament 9. Gas flow 10 is transported through intersection 5 to pressure-regulating device 3 and ultimately to the atmosphere as part of gas flow 12. Upon inspiratory effort by the patient through patient interface device 4, the transient decrease in pressure in respiratory circuit R produces an inspiratory flow 13 to be drawn from circuit P into circuit R and ultimately into the patient's respiratory system through patient interface 4. As shown, inspiratory flow 13 contains at least a portion of the medicament 9 that is entrained in gas flow 10. Expiratory effort by the patient through patient interface 4 produces a transient increase in pressure in respiratory circuit R that moves expiratory flow 14 from the patient interface device through circuit R to circuit P at intersection 5. Expiratory flow 14 joins gas flow 10 in pressure-generating circuit P at intersection 5 to form gas flow 11, which in turn passes through pressure-regulating device 3 to the atmosphere as gas flow 12.

A Bi-level system is similar to system 100, but may employ variable flow valves coupled with pressure sensors to vary the pressure in respiratory circuit R to coincide with the respiratory cycle of the patient. An invasive CPAP system is also similar to system 100, but would employ, for example an endotracheal tube, as the patient interface device 4.

In the embodiment of FIG. 1, the aerosolized medicament may be diluted by the high volume gas flow passing through the pressure-generating circuit, and a portion of the medicament may be ultimately lost to the atmosphere and never reach the patient. The higher the volume of gas flow in the pressure-generating circuit, the smaller the percentage of aerosolized medicament included in the respiratory gas flow to the patient's respiratory system through the patient interface device. For example, an infant breathing a respiratory flow of 0.2 to 0.6 liters/minute from a total flow of 10 liters/minute through the pressure-generating circuit may not be able to inhale more than a small percentage, e.g. from 2-6%, of the aerosolized medicament carried by the flow of gas in the primary pressure-generating circuit.

In one aspect of the present invention, the delivery of aerosolized medicament to a pressure-assisted breathing system is achieved in an efficient manner without the previously-described substantial dilution or loss of medicament. One arrangement may involve an improved CPAP or Bi-level system that introduces an aerosolized medicament directly into the air flow being inhaled by the patient during respiratory therapy and outside the air flow in the primary pressure-generating circuit. Such a CPAP or a Bi-level system may also be configured to employ small amounts of liquid medicament per treatment, for example a unit dose of 4 ml or less. Also, such CPAP or Bi-level systems may utilize a nebulizer having a small, low volume reservoir, thereby providing to smaller patients an efficient method of respiratory therapy using a CPAP or Bi-level system.

Referring now to FIG. 2, one embodiment of an apparatus for applying CPAP in accordance with the present invention will be described. Elements in FIG. 2 that are similar to those in FIG. 1 are assigned the same reference numerals.

CPAP system 200 includes a primary pressure-generating circuit P and a respiratory circuit R. As used herein, the term "circuit" is intended to mean a gas communication path between two points. Circuit P includes a flow generator 2 in gas communication with a pressure regulating device 3. Circuit R includes a patient interface device 4 in gas communication with circuit P at junction 5. In contrast to the CPAP system 100 illustrated in FIG. 1, nebulizer 6 of CPAP system 200 communicates with circuit R at intersection 15 outside pressure-generating circuit P. During operation of CPAP system 200, a high volume flow of gas 8 is introduced into circuit P from flow generator 2 and passes to and through pressure regulating device 3 so as to maintain a positive pressure in the system. Upon inspiratory effort by the patient through patient interface device 4, there is a transient decrease in pressure in circuit R that causes a inspiratory flow 18 to be drawn from circuit P into circuit R and ultimately into the patient's respiratory system through patient interface 4. Nebulizer 6 emits aerosolized medicament 9 into inspiratory flow 18 at junction 15 to produce gas flow 19 in which medicament 9 is entrained and which is carried through patient interface device 4 into the patient's respiratory system. In this way, medicament 9 is emitted only into the flow of gas being inhaled by the patient, thereby greatly increasing the efficiency of delivery of medicament 9 to the patient. Expiratory effort by the patient through patient interface 4 produces a transient increase in pressure that moves expiratory flow 14 from the patient interface device through circuit R to circuit P at junction 5. Expiratory flow 14 joins gas flow 8 at junction 5 to form gas flow 16, which in turn passes through pressure-regulating device 3 as gas flow 17 to the atmosphere. As graphically illustrated in FIG. 2, a greater proportion of medicament 9 is delivered directly to the patient by CPAP system 200 with a lesser amount of dilution and loss into the atmosphere than in CPAP system 100.

Figure 3:
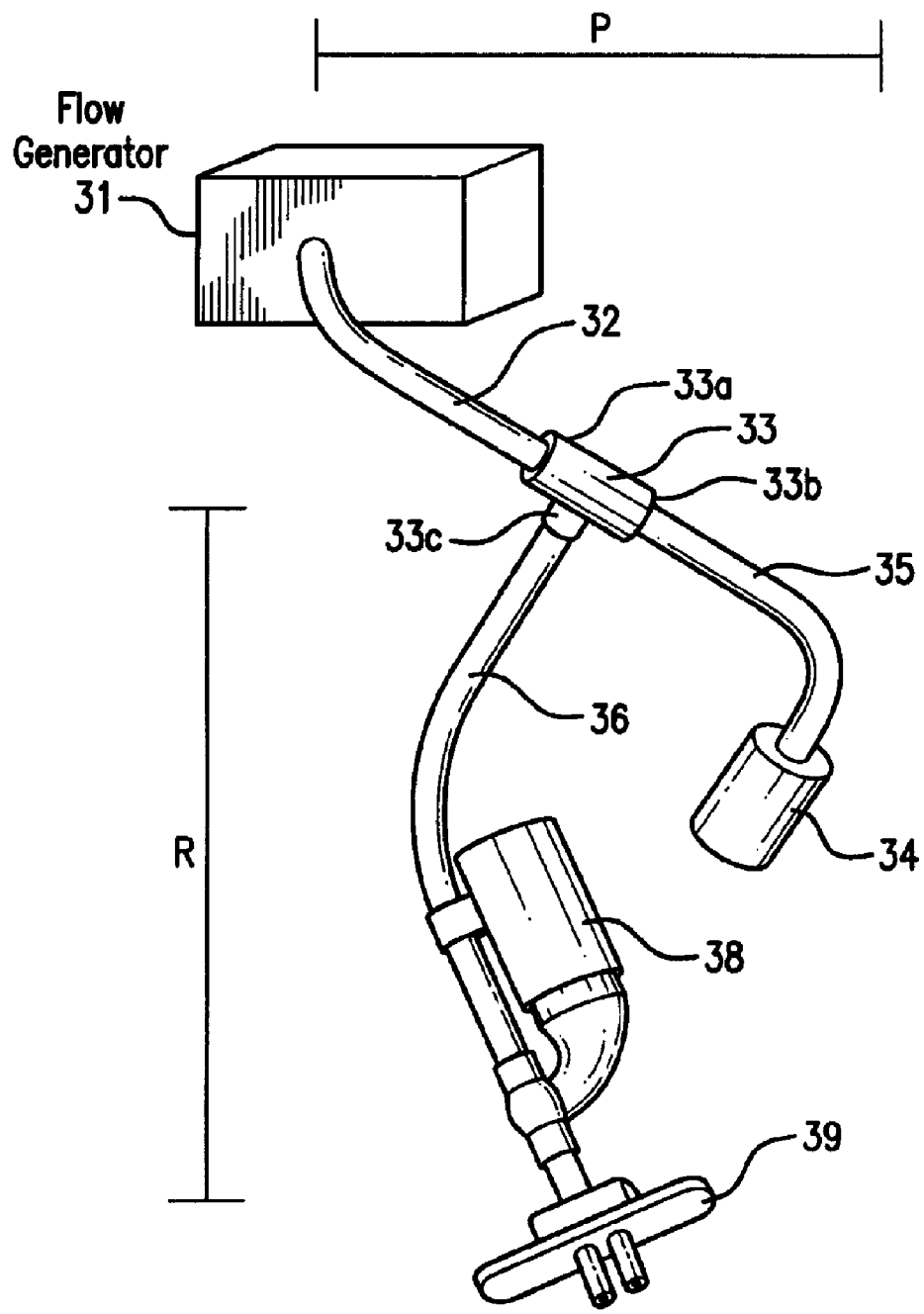
FIG. 3 is a perspective view of a CPAP apparatus of the present invention.

FIG. 3 illustrates an embodiment of the present invention that is particularly suited for use in neo-natal and infant CPAP therapies. Referring now to FIG. 3, the primary pressure-generating circuit P may comprise a gas conduit, e.g. flexible tube 32, that receives the high-volume flow of gas generated by flow generator 31. Flexible tube 32 conducts the flow of gas through junction unit 33 to flexible tube 35, which continues to transport the flow of gas to pressure-regulating device 34. Pressure-regulating device 34 may be connected to a controller (not shown) that regulates the pressure in the system to the desired CPAP. Respiratory circuit R may comprise a gas conduit, e.g. flexible tube 36, that connects with nebulizer 38, which is connected to patient interface device 39, either directly (as shown) or through a short section of flexible tube 36. As previously described, nebulizer 38 is preferably placed in close proximity to patient interface device 39.

Flexible tube 36 is preferably relatively thin, smaller in diameter and more flexible than flexible tubes 32 and 35. For example, flexible tube 36 may be commercially available silicone tubing having an outside diameter of about 5 mm. The more flexible nature of flexible tube 36 allows the patient's head to more freely move about without disconnecting the patient interface device 39 from the patient.

Flow generator 31 may conveniently comprise any of the known sources of pressurized gas suitable for use with pressure-assisted breathing systems such as CPAP or Bi-level. Typically, the flow generator is capable of supplying a flow of high-volume gas, which includes at least some portion of oxygen, at slightly greater than atmospheric pressure. For example, the source of pressurized gas may be an air blower or a ventilator (as shown in FIG. 3), or the pressurized gas may originate from a wall supply of air and/or oxygen, such as that found within hospitals and medical facilities, or may originate from a pressurized cylinder or cylinders. The pressurized gas may comprise various known mixtures of oxygen with air, nitrogen, or other gases and may be provided in a single stream or flow to circuit R, for example, as shown by element 8 of FIG. 2.

Pressure-regulating device 34 may comprise any of the known devices for controlling and maintaining air pressure within a CPAP or Bi-level system at the desired level. Typically, pressure-regulating device 34 may comprise a restrictive air outlet device such as a pressure valve or threshold resistor that modulates the flow of gas leaving the pressure-regulating circuit P. This resistance to air flow may be varied so that the continuous positive airway pressure conducted by respiratory circuit R to patient interface device 39 will suit the needs of the particular patient using the apparatus. Although pressure-regulating device 34 is typically placed downstream of junction unit 33, it may also be placed at or upstream to junction 33.

Junction unit 33 is the point at which respiratory circuit R is in gas communication with primary pressure-generating circuit P. Junction unit 33 preferably comprises a "T" or "Y"-shaped hollow unit (sometimes referred to as the "WYE") to which flexible tubes 32, 35 and 36 are coupled. As shown in FIG. 3, junction unit 33 may comprise an inlet arm 33a and an outlet arm 33b, which together define a primary gas conduit through the body of junction unit 33. Respiratory arm 33c defines a branch gas conduit that depends from and is in gas communication with the primary gas conduit. Flexible tube 32 from flow generator 31 is coupled to the upstream opening in inlet arm 33a and flexible tube 35 leading to pressure-regulating device 34 is coupled to the downstream opening in outlet arm 33b to form pressure-generating circuit P. Flexible tube 36 is coupled to the downstream opening of respiratory arm 33c and, together with patient interface device 39, forms respiratory circuit R.

Patient interface device 39 is coupled to nebulizer 38, either directly (as shown) or through a short section of flexible tube of the same size and material as tubing 36. Patient interface device may include any of the known devices for providing gas communication between the CPAP device and the patient's respiratory system. By way of example, the patient interface device may include nasal prongs (as shown), an oral/nasal mask, a nasal mask, nasopharyngeal prongs, an endotracheal tube, a tracheotomy tube, a nasopharyngeal tube, and the like.

Nebulizer apparatus 38 is disposed in respiratory circuit R between primary pressure-generating circuit P and patient interface device 39 so as to emit an aerosolized medicament into the flow of gas in respiratory circuit R that is inhaled by the patient. Vibrating aperture-type nebulizer apparatus are preferred for the practice of this invention, for example, as described in detail in U.S. Pat. No. 6,615,824, issued Sep. 9, 2003, and in copending U.S. patent application Ser. Nos. 10/465,023, filed Jun. 18, 2003, and Ser. No. 10/284,068, filed Oct. 30, 2002. The entire disclosures of said patent and applications are incorporated herein.

Figure 4:
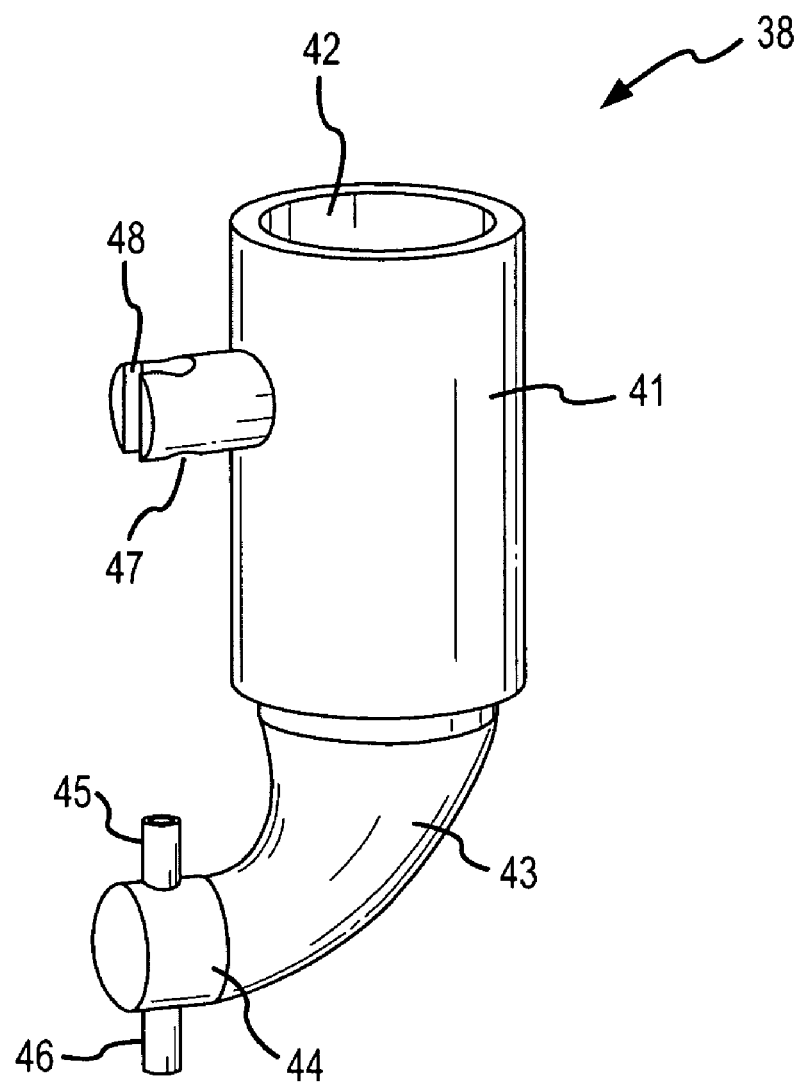
FIG. 4 is a perspective view of a nebulizer apparatus of the present invention

A particularly preferred nebulizer apparatus is the "miniature" nebulizer 38 illustrated in FIG. 4. Nebulizer 38 may comprise a cylindrical body 41 having relatively small dimensions, e.g. about 15 mm in outside diameter and about 20 mm in length. Body 41 may have an upper medicament port 42 at one end and may be coupled to a generally L-shaped arm 43 at the other end. At its distal end, arm 43 includes a generally "I"-shaped connector unit 44 having an inlet nipple 45 and outlet nipple 46. As illustrated in FIG. 3, connector 93 may be used to connect nebulizer 38 to respiratory circuit R by slipping the downstream end of tube 36 over inlet nipple 45 and attaching the patient interface device 39 directly to outlet nipple 46 or through a short section of tube 36. Body 41 may also include a clip holder 47 including notched channel 48, which is adapted to clip over flexible tube 36 to further secure and support nebulizer 38 on tube 36. Nebulizer 38 is preferably light-weight, for example, having a net weight (without contained liquid) of 5 gms or less, most preferably 3 gms or less. Particularly preferred nebulizers of the present invention have a net weight of 1-2 gms.

Figure 5:
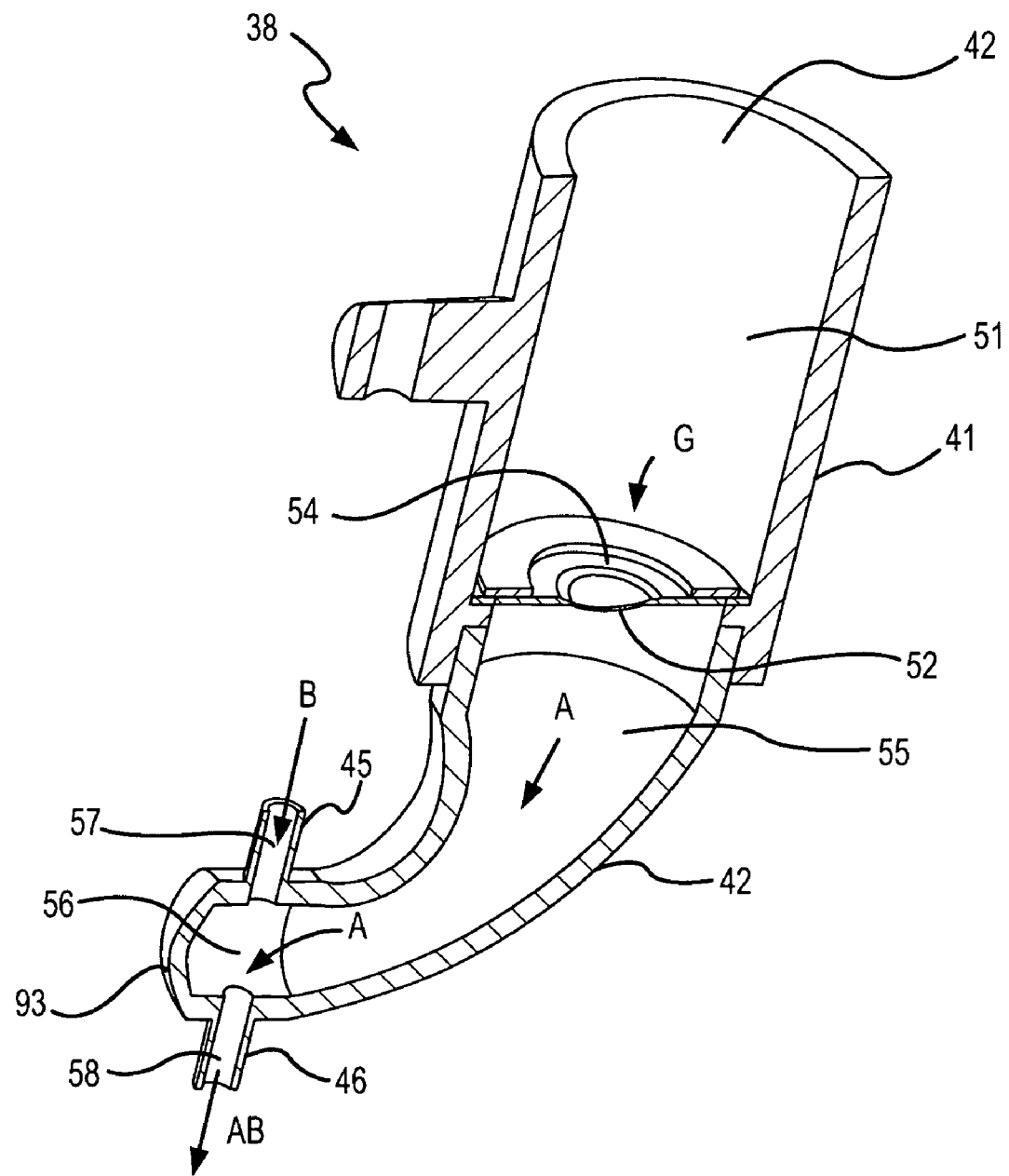
FIG. 5 is a side, cross-sectional view of the nebulizer apparatus of FIG. 4.

Referring now to FIG. 5, nebulizer 38 may comprise a reservoir 51 within cylindrical body 41 for holding a liquid medicament to be delivered to patient's respiratory system and a vibrating aperture-type aerosol generator 52 for aerosolizing the liquid medicament. Upper medicament port 42 may be provided for delivering the liquid medicament into reservoir 51 and a removable plug (not shown) may be provided to seal medicament port 42. Reservoir 51 may be sized to accommodate a small volume of medicament, e.g. a volume of 4 ml or less, and preferably a volume of 1-3 ml. Aerosol generator 52 may be positioned at lower medicament outlet 54 of reservoir 51 so that the liquid medicament flows by gravitational action from the reservoir 51 to aerosol generator 52 (Flow G).

Aerosol generator 52 may comprise a piezoelectric element and a vibratable member having a plurality of tapered apertures extending between a first surface and a second surface thereof. Representative vibratable aperture-type aerosol generators are described in detail in U.S. Pat. Nos. 5,164,740; 5,586,550; 5,758,637; and 6,085,740, the entire disclosures of which are incorporated herein by reference. In general, the first surface of the vibratable member, which faces upwardly, receives the liquid medicament from reservoir 51, and the aerosolized medicament is generated at the second surface of the vibratable member when droplets of medicament are ejected from the apertures upon vibration of the vibratable member. Aerosol generators of the present invention are preferably small and light-weight, for example, about 1 gm.

Aerosol generator 52 is positioned so as to facilitate flow of liquid medicament from the reservoir 51 to the aerosol generator 52 and to facilitate passage of the aerosolized medicament from the aerosol generator 52 into arm 42. Arm 42 may comprise a supply conduit 55 in fluid communication with aerosol generator 52 at one end and connector unit 93 at the other end so as to conduct a flow of aerosolized medicament (Flow A) toward connector 93. Connector 93 may comprise a gas conduit 56, which is defined on one end by inlet conduit 57 in inlet nipple 45 and at the other end by outlet conduit 58 in outlet nipple 46. The gas conduit 56 of connector 93 may be quit small, e.g. less than 10 cc in volume for infant applications, thereby decreasing dead space in the respiratory circuit.

The downstream end of flexible tubing 36 (FIG. 3) may be coupled to inlet nipple 45 of connector 93 to conduct gas flow B in the respiratory circuit into inlet conduit 57 to gas conduit 56 of connector 93. Flow A of aerosolized medicament in supply conduit 55 passes into gas conduit 56 of connector 96 and the aerosolized medicament is entrained in gas conduit 56 with Flow B. The entrained mixture of aerosolized medicament and gas (Flow AB) then passes out of the gas conduit 56 through outlet conduit 58 in outlet nipple 46 and on to the respiratory system of the patient.

Nebulizer apparatus 38 may be connected to a controller (not shown) for controlling operation of and to supply power to the aerosol generator. Preferably, the controller and other electronic components are connected with wires, cables and connectors that are small and flexible. Examples of other components that may also be associated with nebulizer apparatus 38 are a timer, status indication means, liquid medicament supply nebule or syringe, etc., all as known by those skilled in the art and described in detail in the aforementioned patent and patent applications.

The present invention is particularly useful in respiratory therapies that utilize surfactant medicaments. Such surfactants are protein-lipid compositions, e.g. phospholipids, that are produced naturally in the lungs and are essential to the lungs' ability to absorb oxygen. They facilitate respiration by continually modifying surface tension of the fluid normally present within the air sacs, or alveoli, that line the inside of the lungs. In the absence of sufficient surfactant, these air sacs tend to collapse, and, as a result, the lungs do not absorb sufficient oxygen. Insufficient surfactant in the lungs results in a variety of respiratory illnesses in both adults and humans. Since most of these surfactant medicaments are animal-based, the current supply is limited, and although synthetic surfactants are available, their manufacture is both inexact and expensive. In addition, the surfactant medicaments are typically high in viscosity and are difficult to deliver to the patient's respiratory system. The increased efficiency of the pressure-assisted breathing system of the present invention, and the smaller amount of medicament required for a treatment according to the present invention, can be a substantial advantage when such scarce and expensive medicaments are employed.

In a preferred embodiment, the nebulizer of the present invention has a reservoir capacity equal to a unit dose of medicament. As an example, one dose of a liquid phospholipid surfactant medicament is typically achieved by instilling about 100 mg of the surfactant into an infant's lung. However, the required aerosol dose appears to be considerably less. For example, animal researchers have determined that an inhaled dose of about 4.5 mg/kg of surfactant is sufficient to substantially improve oxygenation in animal models. This suggests that a sufficient unit dose of surfactant to deliver to the lungs of a 1 kg. infant in aerosolized form may be about 5-10 mg. Since liquid surfactant is typically dispensed in a dilute solution having a concentration of 25 mg/ml, about 2/5 ml (10/25 ml) of liquid surfactant may be required to obtain 10 mg of active surfactant. A neonate CPAP system may be designed according the present invention to deliver about 6-18% of the total aerosolized medicament to an infant's lungs with a normal breathing pattern. If, for example, the nebulizer efficiency is 10%, the amount of surfactant solution required in the nebulizer reservoir to deliver a unit dose of aerosolized surfactant would have to be increased by a factor of 10, i.e. 10×2/5 ml or 4 ml. Therefore, a nebulizer reservoir having a capacity of 4 ml may be sufficient to provide a unit dose of surfactant to a 1 kg infant in accordance with the present invention without the need to replenish the reservoir.

The unit dose and the corresponding nebulizer reservoir size may vary depending on the efficiency of the nebulizer, the weight of the patient and the amount of surfactant needed. For example, if the infant in the above example weighs 3 kg, a unit dose (and corresponding reservoir size) would be about 12 ml of liquid surfactant (i.e. 3 kg×4 ml/kg). Similarly, if 5 mg of active surfactant is needed in the above example, a unit dose would be about 2 ml of liquid surfactant (i.e. 5/25 ml×10), and if the efficiency of the nebulizer in the above example is 15%, a unit dose would be about 2 2/3 ml (i.e. 2/5 ml×100/15).

A nebulizer according to the present invention may administer a unit dose by aerosol in less than 20 minutes, and possibly in as little as 5 minutes. Aerosol generation can be continuous or phasic, and can be timed to titrated dose delivery rate over time; for example, a 4 ml maximum dose with nebulization for 1 second out of every 10, 20 or 30 seconds.

Figure 6:
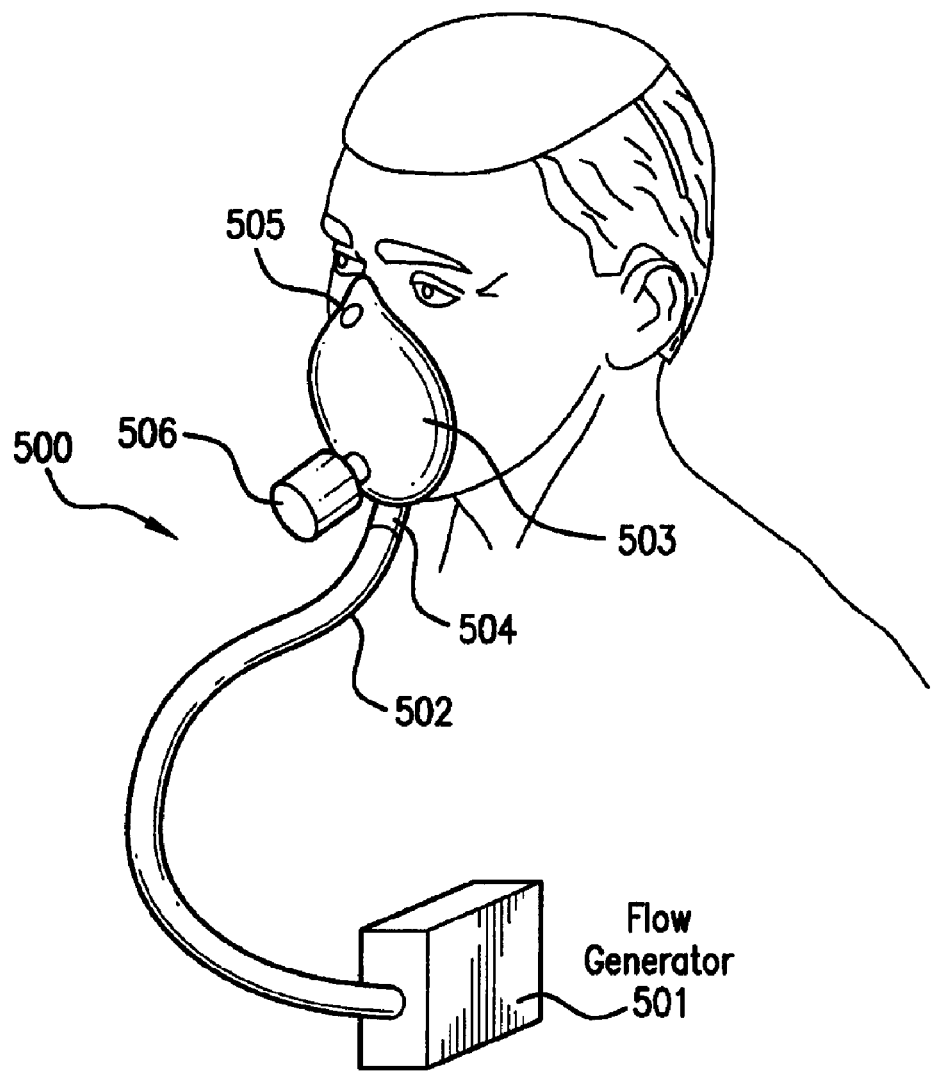
FIG. 6 is a perspective view of a mask CPAP apparatus of the present invention.

The miniature vibrating aperture-type nebulizer apparatus of the present invention is so small and quiet that it may be placed in very close proximity to the mouth, nose or artificial airway of the patient. This placement further ensures that the aerosolized medicament is introduced directly into the flow of gas being inhaled by the CPAP patient (i.e. into the respiratory circuit) and eliminates the dilution effect caused by introducing the medicament into the high-volume flow of gas from the flow generator (i.e. in the pressure-generating circuit). FIG. 6 illustrates a typical adult CPAP/Bi-level system comprising a flow generator 501 attached by a single flexible tube 502 to a nasal or full face mask 503. Pressure is maintained by a flow of gas escaping through a fixed orifice located in swivel valve 504 between the tube 502 and the mask 503. In an alternative embodiment, a fixed orifice 505 may be located at the top (above the bridge of the nose) of the mask 503. In both embodiments, the entire respiratory circuit R is contained within the patient interface device. Nebulizer apparatus 506 is coupled to mask 503 so that the aerosolized medicament exits the nebulizer apparatus into the respiratory circuit directly in the vicinity of the mouth and nose of the patient. In this manner, the efficiency of the system is increased by decreasing the distance which the aerosolized medicament must travel, i.e. by decreasing the length of the respiratory circuit. In an alternative embodiment, the aerosol generator can be operated only during patient inspiration, further improving the efficiency of the system.

Figure 7:
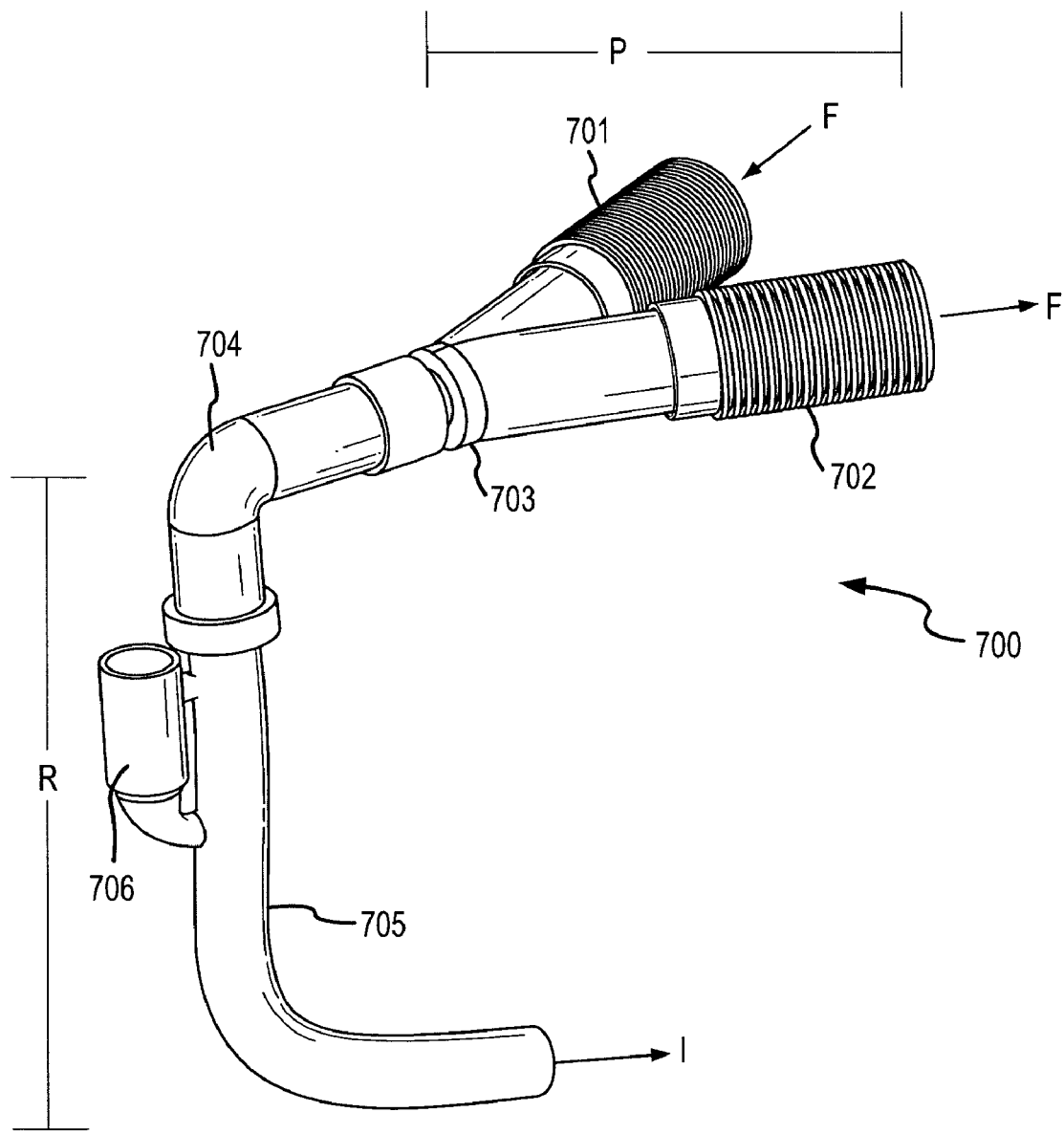
FIG. 7 is a perspective view of an alternative CPAP arrangement in accordance with the present invention.

FIG. 7 illustrates another alternative embodiment of the invention suitable for adults. CPAP apparatus 700 comprises flexible tube 701 conducting gas flow F from a flow generator (not shown) through "Y"-shaped junction unit 703 and flexible tubing 702 to a pressure-regulating device (not shown) to form pressure-generating circuit P. Elbow-shaped junction unit 704 connects pressure-generating circuit P to respiratory circuit R at junction unit 703. Respiratory circuit R comprises a smaller flexible tubing 705 which conducts gas flow I from elbow unit 704 to a patient interface device (not shown). Nebulizer apparatus 706 is disposed on tubing 705 so as to entrain aerosolized medicament into gas flow I being inhaled by the patient, as previously described above.

It is understood that while the invention has been described above in connection with preferred specific embodiments, the description and drawings are intended to illustrate and not limit the scope of the invention, which is defined by the appended claims and their equivalents.

What is claimed is:

1. A method of delivering a surfactant to a patient's respiratory system which comprises the steps of:
providing a CPAP system having a pressure-generating circuit with a first gas flow of sufficiently high volume to maintain continuous positive airway pressure in the system, a respiratory circuit connecting the pressure-generating circuit to a patient interface device, wherein the respiratory circuit contains a second gas flow of lower volume than said first gas flow, and a vibrating aperture nebulizer coupled to the respiratory circuit at a distance from the patient interface device sufficient to provide an acceptable efficiency of delivering a liquid surfactant to the patient's respiratory system;
introducing the liquid surfactant into the nebulizer;
aerosolizing the surfactant in the nebulizer; and
entraining the aerosolized surfactant into the second gas flow of the respiratory circuit to avoid dilution of the aerosolized surfactant delivered to the patient.

2. The method of claim 1 wherein the surfactant is a phospholipid.

3. The method of claim 1 wherein 6-18% of the aerosolized surfactant introduced into the system is delivered to the patient.

4. The method of claim 1 wherein the nebulizer comprises a reservoir having a capacity substantially equal one unit dose of surfactant and substantially all of the contents of the reservoir is delivered to the patient.

5. The method of claim 1 wherein the dose is equal to 10 mg or less of surfactant.

6. The method of claim 1 wherein the patient interface device is selected from the group consisting of nasal prongs, an oral/nasal mask, a nasal mask, nasopharyngeal prongs, a nasopharyngeal tube, a tracheotomy tube, an endotracheal tube and a mouthpiece.

7. The method of claim 6 wherein the patient interface device is an endotracheal tube.

* * * * *